(12) United States Patent
Jankowski et al.

(10) Patent No.: US 9,681,872 B2
(45) Date of Patent: Jun. 20, 2017

(54) VACUUM ASSISTED SURGICAL STAPLER (71) Applicant: Covidien LP, Mansfield, MA (US)

(72) Inventors: Bruce Jankowski, Meriden, CT (US); Joseph Richard Wittman, Weissenfeld (DE)

(73) Assignee: Covidien LP, Mansfield, MA (US)

(*) Notice: Subject to any disclaimer, the term of this patent is extended or adjusted under 35 U.S.C. 154(b) by 490 days.

(21) Appl. No.: 14/294,647

(22) Filed: Jun. 3, 2014

(65) Prior Publication Data
US 2014/0263573 A1 Sep. 18, 2014

Related U.S. Application Data

(60) Continuation of application No. 13/571,290, filed on Aug. 9, 2012, which is a division of application No. (Continued)

(51) Int. Cl.
*A61B 17/064* (2006.01)
*A61B 17/068* (2006.01)
(Continued)

(52) U.S. Cl.
CPC ........ *A61B 17/0682* (2013.01); *A61B 17/072* (2013.01); *A61B 17/115* (2013.01);
(Continued)

(58) Field of Classification Search
CPC A61B 2017/07257; A61B 2017/07271; A61B 2017/081; A61B 17/064
(Continued)

(56) References Cited

U.S. PATENT DOCUMENTS 4,319,576 A 3/1982 Rothfuss
4,350,160 A 9/1982 Kolesov et al.
(Continued)

FOREIGN PATENT DOCUMENTS

WO 0238037 A2 5/2002
WO 03/053255 A1 7/2003

OTHER PUBLICATIONS

European Search Report EP 03814347 dated Jul. 20, 2007.
PCT International Search Report for International Application No. PCT/US2003/041068 dated Jul. 19, 2004.

*Primary Examiner* — Gloria R Weeks (57) ABSTRACT

A surgical stapling apparatus having a vacuum device associated therewith is disclosed. The vacuum device may be removable, fixedly secured thereto, or incorporated into the surgical stapling apparatus. The vacuum device may include a resilient band and vacuum tube secured to the shell assembly or body portion of the surgical stapling apparatus. Alternately, a vacuum chamber may be secured about the shell assembly and/or body portion of the stapling apparatus. In addition, one or more vacuum tubes may be positioned in the vacuum chamber. The vacuum tubes, preferably, extend into the shell assembly and are movable between nondeployed and deployed positions such that a distal end of each tube can be selectively positioned at multiple positions 122 between the shell assembly and an anvil. The vacuum tubes can be formed of a shape-memory material such that the tubes point radially outwardly of the shell assembly when the tubes are in the deployed position.

15 Claims, 11 Drawing Sheets

Related U.S. Application Data

10/540,197, filed as application No. PCT/US03/41068 on Dec. 22, 2003, now Pat. No. 8,328,060.

(60) Provisional application No. 60/435,223, filed on Dec. 20, 2002.

(51) Int. Cl.
  *A61B 17/072* (2006.01)
  *A61B 17/115* (2006.01)
  *A61B 17/30* (2006.01)

(52) U.S. Cl.
  CPC . *A61B 17/1155* (2013.01); *A61B 2017/07214* (2013.01); *A61B 2017/306* (2013.01)

(58) Field of Classification Search
  USPC .......................................... 227/175.1, 176.1
  See application file for complete search history.

(56) References Cited

U.S. PATENT DOCUMENTS

| | | | |
|---|---|---|---|
| 4,602,634 A * | 7/1986 | Barkley | ............. A61B 17/0643 227/178.1 |
| 4,893,622 A | 1/1990 | Green et al. | |
| 4,990,153 A | 2/1991 | Richards | |
| 5,104,394 A * | 4/1992 | Knoepfler | ........... A61B 17/1285 227/180.1 |
| 5,119,983 A | 6/1992 | Green et al. | |
| 5,271,544 A | 12/1993 | Fox et al. | |
| 5,282,807 A | 2/1994 | Knoepfler | |
| 5,322,161 A | 6/1994 | Shichman et al. | |
| 5,395,030 A | 3/1995 | Kuramoto et al. | |
| 5,503,635 A | 4/1996 | Sauer et al. | |
| 5,542,949 A | 8/1996 | Yoon | |
| 5,582,611 A | 12/1996 | Tsuruta et al. | |
| 5,827,323 A | 10/1998 | Klieman et al. | |
| 5,839,639 A | 11/1998 | Sauer et al. | |
| 5,915,616 A | 6/1999 | Viola et al. | |
| 6,083,241 A | 7/2000 | Longo et al. | |
| 6,193,129 B1 | 2/2001 | Bittner et al. | |
| 6,241,140 B1 | 6/2001 | Adams et al. | |
| 6,506,196 B1 | 1/2003 | Laufer | |
| 6,575,971 B2 | 6/2003 | Hauck et al. | |
| 6,601,749 B2 | 8/2003 | Sullivan et al. | |
| 6,632,227 B2 | 10/2003 | Adams | |
| 6,695,866 B1 | 2/2004 | Kuehn et al. | |
| 7,094,244 B2 | 8/2006 | Schreck | |
| 7,097,650 B2 | 8/2006 | Weller et al. | |
| 7,694,864 B2 | 4/2010 | Okada et al. | |
| 7,914,543 B2 | 3/2011 | Roth et al. | |
| 8,590,764 B2 * | 11/2013 | Hartwick | ......... A61B 17/00234 227/179.1 |
| 8,663,241 B2 * | 3/2014 | Adams | ............. A61B 17/07207 227/131 |
| 2002/0082621 A1 | 6/2002 | Schurr et al. | |
| 2004/0217146 A1 | 11/2004 | Beck | |
| 2009/0125040 A1 | 5/2009 | Hambly et al. | |

\* cited by examiner

VACUUM ASSISTED SURGICAL STAPLER

CROSS-REFERENCE TO RELATED APPLICATIONS

This application is a Continuation of U.S. patent application Ser. No. 13/571,290 filed Aug. 9, 2012, which is a Division of U.S. patent application Ser. No. 10/540,197 filed Jun. 20, 2005, now U.S. Pat. No. 8,328,060, which is a National State Entry under 35 U.S.C. §371 of International Application No. PCT/US03/41068 filed Dec. 22, 2003, which claims benefit of, and priority to, U.S. Provisional Application No. 60/435,223 filed Dec. 20, 2002, and the disclosures of each of the above-identified applications are hereby incorporated by reference in their entirety.

BACKGROUND

1. Technical Field

The present disclosure relates to surgical instruments, e.g., surgical fastener or stapler apparatus and, more particularly to circular surgical staplers for performing surgical procedures, including but not limited to rectal mucosectomies, rectal anopexies, anastamoses, hemorrhoidectomies, or the like. In addition the present disclosure relates to methods of performing such surgical procedures.

2. Background of Related Art

Various types of surgical fastener applicators and/or staplers are known for the application of fasteners or staples to tissue in order to join adjacent tissues. For example, it is known to use various types of staplers in gastric and esophageal surgery, in both classic or modified gastric reconstructions performed end-to-end, end-to-side, or side-to-side, as well as for performing a hemorrhoidectomy.

Hemorrhoids are a mass of dialated veins in swollen tissue at the margin of the anus or nearby within the rectum. Typically, hemorrhoids are caused by chronic straining for example from constipation and/or childbirth. The plexus of vascular tissue beneath the epithelial lining of the anal canal is called the corpus cavemosus recti or anal cushion. The plexus connect arteries to veins without intervening capillaries thus creating the vascular component of the anal cushions. These arteriovenous channels control the size of the anal cushions by regulating the blood volume flowing through them. Chronic straining damages the submucosal fibroelastic connective and the anal cushions protrude into the anal canal and may produce painless bleeding (first degree hemorrhoids). Prolapsed hemorrhoids lying outside the anal canal may become strangulated by the internal sphincter activity with possible thrombosis of the venous plexus (fourth-degree hemorrhoids). This condition may result in gangrene with the risk of abscess formation.

Hemorrhoids can be of two types, external and internal. A ribbed dentate line is located about 2.5 to 3 cm in from the exterior of the anus and marks the change from the anus to the rectum. Hemorrhoids are found in the anal area before this line. Internal hemorrhoids generally are found in the rectal area before this line and external hemorrhoids generally are external of the anal ring. Internal hemorrhoids are generally formed from arteriovenous anastomoses or connections that reside in a submucosal space within the wall of the rectum, approximately 2.5 to 5 cm in from the exterior of the anus. Due to its proximity to the anus, internal hemorrhoids can protrude from the wall of the rectum in either one localized area, more than one localized area, or circumferentially around the rectum and in certain severe cases, the internal hemorrhoids can protrude out of the anus.

A wide variety of surgical methods have been suggested for the treatment of severe internal hemorrhoids. One method is a closed hemorrhoidectomy. According to this method a retractor is inserted into the anus to obtain access to a hemorrhoidal site. The surgeon then clamps the hemorrhoid with alligator clamps, ligates the vessels, and dissects the hemorrhoid from the rectal wall with a scalpel or scissors. Once the hemorrhoid is removed, the surgical site is sutured closed. The retractor is then rotated to another position and the remaining hemorrhoids are treated in a similar manner until all of the hemorrhoids have been removed.

Another method for the removal of internal hemorrhoids is an open hemorrhoidectomy. According to this procedure, rather than using a retractor, the anus is gently dilated with two fingers and forceps are placed at the mucocutaneous junction of each primary hemorrhoid. The hemorrhoids are pulled down and a second forceps is applied to the main bulk of each hemorrhoid to produce "a triangle of exposure". Next, the clamped, hemorrhoid is dissected from the sphincter muscle and is dissected proximally as far as the pedicles and then ligated or tied. Unlike the closed procedure, the wound is not sutured closed, but is left open with a light dressing applied to the wound.

Yet another hemorrhoidectomy procedure involves excising hemorrhoidal tissue above the dentate line and excising and suturing the redundant rectal mucosa to the anoderm. This procedure is particularly used in conjunction with circumferential hemorrhoids.

In a paper by Dr. G. Allegra entitled "Particular Experience with Mechanical Sutures: Circular Stapler for Hemorrhoidectomy," presented to the 1.sup.st. National Conference of the Italian Viscerosynthesis Association in May 28-30, 1989, and published in GIORN Chir. Vol. 11-No. 3-pp 95-97, March 1990, Dr. Allegra disclosed a simpler and faster method for performing a hemorrhoidectomy. The paper discloses the use of a conventional circular stapler to perform a hemorrhoidectomy on second and third degree hemorrhoids. According to the procedure detailed by Dr. Allegra, the anus is dilated to place a continuous submucosal circle of sutures at the base of the pectinate or dentate line. Next, the end effector of a conventional circular stapling instrument is opened and placed into the anus of a patient such that the anvil assembly of the stapling end effector is distal of the suture ring and the stapling head assembly (of the stapling end effector) is proximally outside of the patient. This placement enables the surgeon to reach within the anus in order to grasp the loose ends of the suture. The loose ends of the suture are then pulled to draw the circle of suture closed and to draw the hemorrhoidal tissue in around the anvil shaft which connects the anvil to the stapling head assembly of the circular stapling instrument. Next, the surgeon closes the anvil upon the hemorrhoidal mass and the stapler is fired to perform the hemorrhoidal transection. Once fired, the circular stapling instrument is removed from the anus with the transected hemorrhoids captured within.

One limitation of Dr. Allegra's procedure is that the stapling head assembly must be placed proximally outside of the patient to enable the surgeon to grasp the loose ends of the suture and to draw the suture out of the anus through a gap between the anus and the stapling head assembly. The gap between the anus and the stapling head assembly is needed to permit withdrawal of the suture from the anus and thus limits the depth that the stapling end effector can be placed into the anus. Using Dr. Allegra's procedure, if the hemorrhoids are located deeper into the anal canal, as in the case of internal hemorrhoids, the stapling head assembly enters the anus and effectively blocks the surgeon from accessing the loose ends of the suture.

An additional limitation of Dr. Allegra's procedure is the amount of hemorrhoidal tissue that can be drawn into the stapling end effector of a conventional circular stapling instrument. Hemorrhoids are drawn into and around an anvil shaft (connecting the open anvil assembly to the stapling head assembly) by tightening a continuous loop of suture placed below the dentate line. This action draws the hemorrhoids around the anvil shaft but does not draw the hemorrhoids into the inner chamber of the stapling head assembly. This limits the amount of hemorrhoidal tissue that can be brought into the stapling end effector and the surgeon may remove only part of a hemorrhoid.

U.S. Pat. No. 6,083,241, to Longo et al. also discloses a method for removing internal hemorrhoids from a patient using a circular stapler. A suture is placed into or above the internal hemorrhoids of the patient. A needle hook is employed to grasp the suture and withdraw the suture through a passageway in the stapling head assembly and out of the casing of the stapling head assembly. The circular stapling instrument is closed and then fired in order to staple and cut the hemorrhoidal tissue and the stapling instrument is removed from the patient to remove the tissue from the patient.

A significant drawback of both the Dr. Allegra and the Longo et al. procedures is the complexity of the procedures. Each calls for the hemorrhoidal tissue to be sutured, prior to stapling and cutting. This significantly increases the time of performing the procedure and in turn increases the potential for complications and the potential for trauma to the patient. As described above, each procedure generally requires that a purse string type suture be first sewn into the tissue by using a retractor to expose a portion of the tissue; suturing the exposed portion of the tissue; repositioning the retractor adjacent the sutured portion and repeating these steps around the circumference of the rectal cavity until the entire tissue has been sutured.

Thus, the need exists for surgical staplers and/or apparatus which are less complex and can more quickly perform a surgical procedure than existing surgical staplers. In addition, the need exists for staplers and/or apparatus which reduce the trauma experienced by the patient during the surgical procedures described above. Further, the need exists for methods of performing the above described surgical procedures which are less complex and less time consuming than existing methods of performing the same.

SUMMARY

In accordance with the present disclosure, a circular surgical stapling apparatus is provided in combination with a vacuum device. The vacuum device may be formed integrally with or incorporated into the surgical stapling apparatus. Alternately, the vacuum device may be removably or fixedly secured to the surgical stapling device.

In one preferred embodiment of the present disclosure, a vacuum device is secured to the shell assembly of a surgical stapling apparatus. The vacuum device may be secured to the shell assembly of a surgical stapling apparatus by a resilient collar or band such that a source of vacuum is communicated with the vent holes in the shell assembly. It is also contemplated that the vacuum device may be secured directly to one or more of the vent holes of the shell assembly or that the vacuum device may include a vacuum chamber positioned about the shell assembly of the surgical stapling apparatus. In another preferred embodiment, one or more vacuum tubes are provided in the vacuum chamber. Each vacuum tube has a first end positioned with the vacuum chamber and a second end positioned within the inner chamber of the shell assembly. Preferably, the first end of each vacuum tube is supported on a slidable manifold which is connected to a remotely located finger actuator. The finger actuator is actuable to reposition the second end of each vacuum tube from a location within the inner chamber of the shell assembly to a position external of the shell assembly.

In yet another preferred embodiment of the present disclosure, means for drawing a vacuum is incorporated into the surgical stapling apparatus. In one preferred embodiment, a vacuum channel is provided through the elongated body and shell assembly of the surgical stapling apparatus. One end of the vacuum channel communicates with vacuum openings formed in the anvil shaft of the surgical stapling apparatus and the other end of the vacuum channel communicates with a source of vacuum may be an external source or a self-contained unit positioned within the surgical stapling apparatus. The vacuum openings in the anvil shaft may have any desired configuration.

BRIEF DESCRIPTION OF THE DRAWINGS

The present disclosure will be further described with reference to the accompanying drawings, wherein like reference numerals refer to like parts in the several views, and wherein.

DETAILED DESCRIPTION OF PREFERRED EMBODIMENTS

Preferred embodiments of the presently disclosed surgical apparatus will now be described in detail with reference to the drawing figures wherein like reference numerals identify similar or identical elements. In the drawings and in the description which follows, the term "proximal", as is traditional will refer to the end of the surgical apparatus which is closest to the operator, while the term "distal" will refer to the end of the device which is furthest from the operator. While the following description of the surgical apparatus and method will relate mainly to the removal of rectal mucosal tissue from a patient, it is envisioned that the apparatus according to the present disclosure is not limited to the removal of the rectal mucosal tissue and can be used to perform additional or other surgical procedures.

In the present disclosure, the term "rectal mucosectomy" is understood to include rectal-cuff-mucosectomy, circular stapler anopexy, hemorrhoidectomy, anastomosis, colonectomy and any other surgical procedure involving the mucosal wall of a lumen of the body. The term "staple" or "fastener" as used in the present disclosure, includes single or multi-part, e.g., two-part, surgical fasteners, surgical staples, and the like.

It is also noted that a variety of circular surgical stapling apparatus are well known. Although the present disclosure illustrates one preferred circular stapling apparatus, it is envisioned that the teachings provided herein may be applied to any of the variety of known stapling apparatus.

Figure 1:
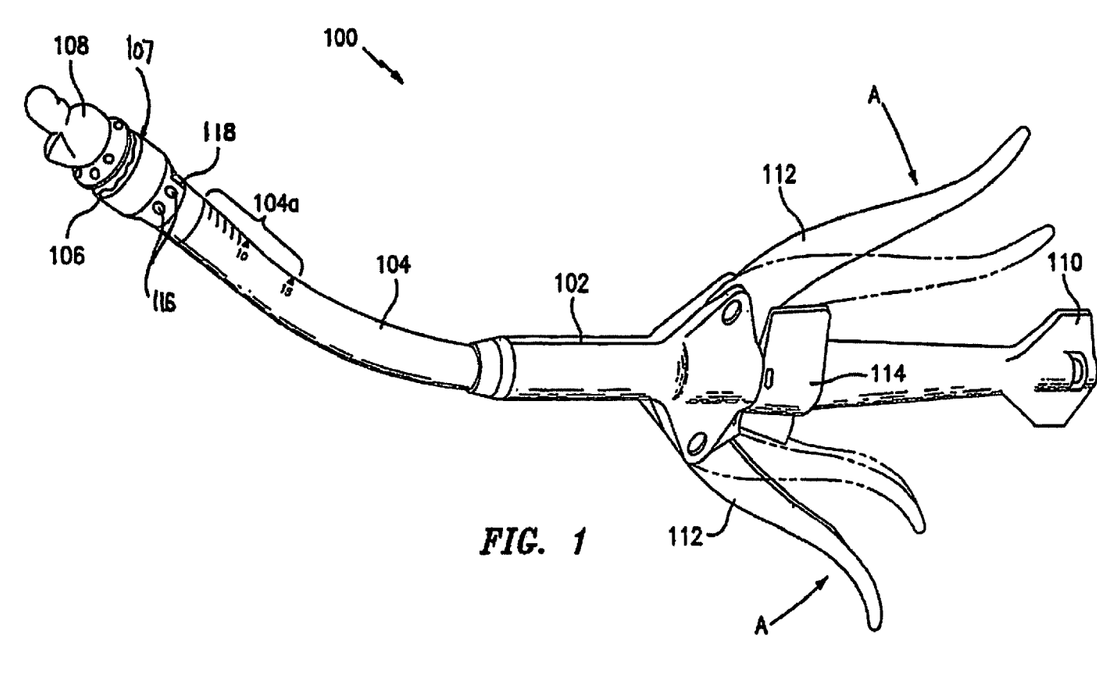
FIG. 1 is a side perspective view of a conventional circular surgical stapling apparatus.

Referring initially to FIG. 1, a surgical stapling apparatus in accordance with the present disclosure is generally designated as 100. Surgical stapling apparatus 100 is of a generally conventional structure and includes a yoke 102, an elongated body 104 extending from yoke 102, a shell assembly 107 configured and adapted to carry a cartridge assembly 106 (FIG. 2) and defining an internal chamber 150 at a distal end thereof, and an anvil assembly 108 at a distal end of the apparatus 100. Apparatus 100 has an approximation mechanism (not shown) extending proximally from anvil assembly 108 through elongated body 104 to a wing nut 110 at a proximal end of apparatus 100, for moving anvil assembly 108 in relation to cartridge assembly 106. In addition, a pair of handles 112 are mounted to apparatus 100, to be manually grasped by the surgeon and moved towards each other as indicated by arrows "A" in FIG. 1, in order to fire staples from cartridge assembly 106 towards anvil assembly 108 and to actuate an annular blade 130 movably positioned within shell assembly 107. A safety lock 114 is also mounted on the proximal end of yoke 102. Safety lock 114 prevents inadvertent movement of handles 112 towards each other to prevent premature firing of the staples or actuation of the annular blade. As is known in the art, one or more suitable venting holes 116 are provided in conical section 118 of shell assembly 107 for venting the interior of cartridge assembly 106. In accordance with one embodiment of the present disclosure, these and/or other vent holes or apertures can be employed or provided for providing a vacuum to the interior or inner chamber 150 (FIG. 2) of shell assembly 107. Other known surgical stapling apparatus are described in commonly assigned U.S. Pat. No. 5,915,616 to Viola et al. and PCT International application No. PCT/US02/10792, filed Apr. 3, 2002, the entire disclosure of each of which is incorporated herein by reference. Copending application entitled "Surgical Stapler Apparatus And Method" filed under Express Mail Mailing Label No. EV149022962US filed on an even date herewith is also incorporated herein by reference in its entirety.

Figures 2, 2A:
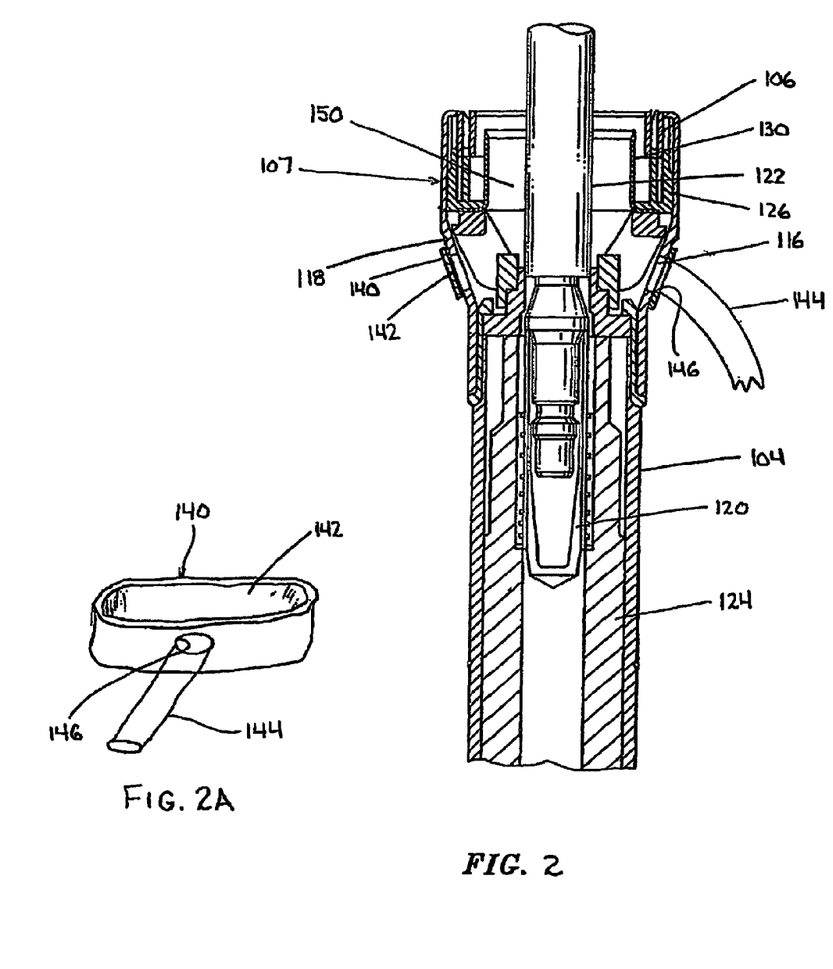
FIG. 2 is a side cross-sectional cutaway view of the distal end of the circular surgical stapling apparatus shown in FIG. 1 with one preferred embodiment of the presently disclosed vacuum device or collar positioned about a portion of shell assembly.
FIG. 2A is a side perspective view of the vacuum collar shown in FIG. 2 with a portion of the vacuum conduit cutaway.

Referring to FIG. 2, generally, circular surgical stapling apparatus include an anvil retainer 120 for securing an anvil shaft 122 of the anvil assembly 108 (FIG. 1) to an approximation mechanism of surgical stapling apparatus 100. The approximation mechanism is actuable, e.g., via wing nut 110, to reciprocate anvil retainer 120 within elongated body 104 and, thus, reciprocate anvil shaft 122 within elongated body 104 and shell assembly 107. Reciprocation of anvil shaft 122 within elongated body 104 effects movement of anvil assembly 108 in relation to shell assembly 107 between spaced and approximated positions. A pusher assembly is also provided which includes a pusher back 124 and a staple driver 126. Pusher back 124 is moved within elongated body 104, e.g., via operation of handles 112, to advance staple driver 126 and annular knife blade 130 through cartridge assembly 106 to eject staplers or fasteners 128 from cartridge assembly 106 and cut tissue.

Referring now to FIGS. 2 and 2A, in one preferred embodiment of the presently disclosed circular stapling apparatus 100, a vacuum device including a resilient or elastic collar or band 140 is provided which includes an annular resilient band body 142 and a flexible vacuum conduit 144. Vacuum conduit 144 has a first end which communicates with a port 146 formed in band body 142. A second end (not shown) of conduit 144 is adapted to communicate with a source of vacuum. Vacuum conduit 144 can be integrally formed with band body 142 or in the alternative secured to band body with a suitable connector, e.g., threads, interlocking structure, etc. Resilient band 142 is preferably formed of an elastomer neoprene or a natural or synthetic rubber, although other resilient and non-resilient materials may be used. Band 142 is dimensioned to be received preferably tightly about conical section 118 of shell assembly 107 such that port 146 of band body 142 communicates with preferably one or more a venting holes 116 and/or other aperture(s) or clearance(s) in shell assembly 107. Remaining venting holes 116 are fluidly sealed by band body 142.

In use, when the distal end of apparatus 100 is positioned within a lumen, e.g., the anus, and a vacuum is drawn through vacuum conduit 114 and port 146 in band body 142, a low pressure region or vacuum is created within inner chamber 150 defined in shell assembly 107. This vacuum or low pressure region causes tissue, e.g., the mucosal wall of the lumen, to be sucked or drawn into inner chamber 150 of shell assembly 107 about anvil shaft 122. Thus, when apparatus 100 is approximated, i.e., anvil shaft 122 is retracted into elongated body 104, tissue is trapped between anvil assembly 108 and cartridge assembly 106. Thereafter, apparatus 100 can be fired in the manner set forth above to staple and sever tissue.

Figure 3:
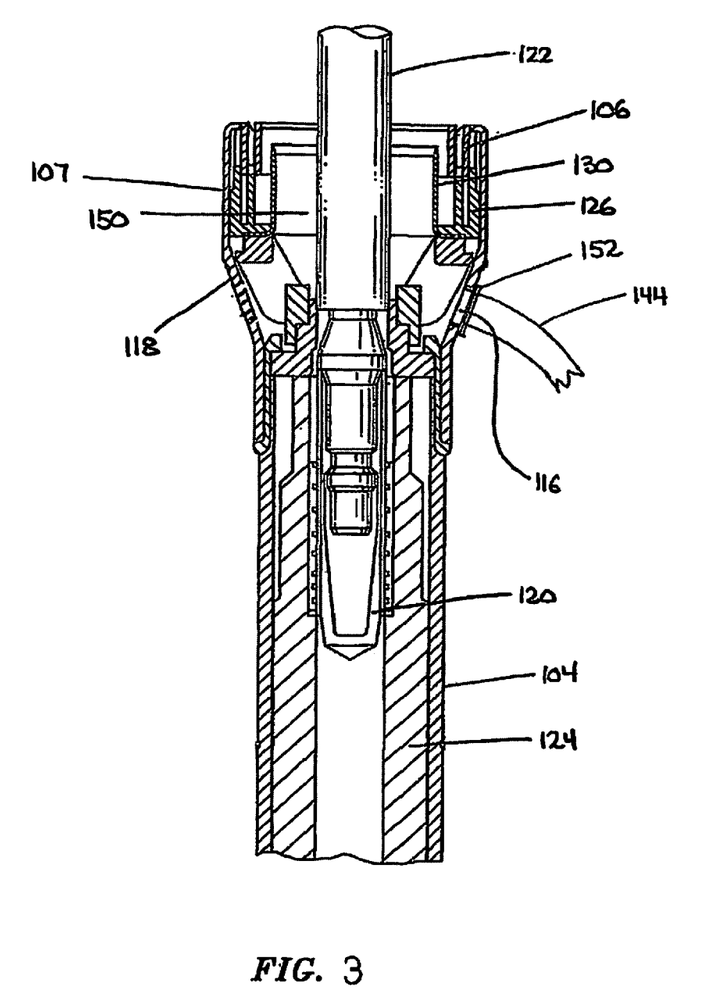
FIG. 3 is a side cross-sectional cutaway view of the distal end of the circular surgical stapling apparatus shown in FIG. 1 with another preferred embodiment of the presently disclosed vacuum device secured to the shell assembly thereof.

Referring to FIG. 3, it is also contemplated that vacuum conduit 144 can be attached to a venting hole and or other apertures or clearances 116 using means other than a resilient band. For example, a connection, e.g., a screw fitting 152, a quick disconnect fitting, a friction fitting, etc., on either or both members to be directly or indirectly connected may be used to attach vacuum conduit 144 to, or communicate with, one or more holes 116 (one shown). The remaining holes 116 can be sealed using any known technique or, in the alternative, apparatus 100 may be provided with only a single hole 116.

FIGS. 4-11 illustrate various alternative embodiments of the presently disclosed circular stapling apparatus, each including a different means for applying or drawing a vacuum in the inner chamber of the shell assembly. Although many of the embodiments illustrated herein include an external vacuum source, it is envisioned that each apparatus described above can be configured and adapted to include a self-contained vacuum unit, e.g., a vacuum unit may be contained within the handle assembly or elongated body of the circular stapling apparatus. Each of the disclosed circular stapling apparatus may also be adapted to be incorporated into a robotically controlled, remotely actuated system. Thus, the vacuum source can be operated remotely or located in a remote unit or control box, as in a robotic system.

Figure 4:
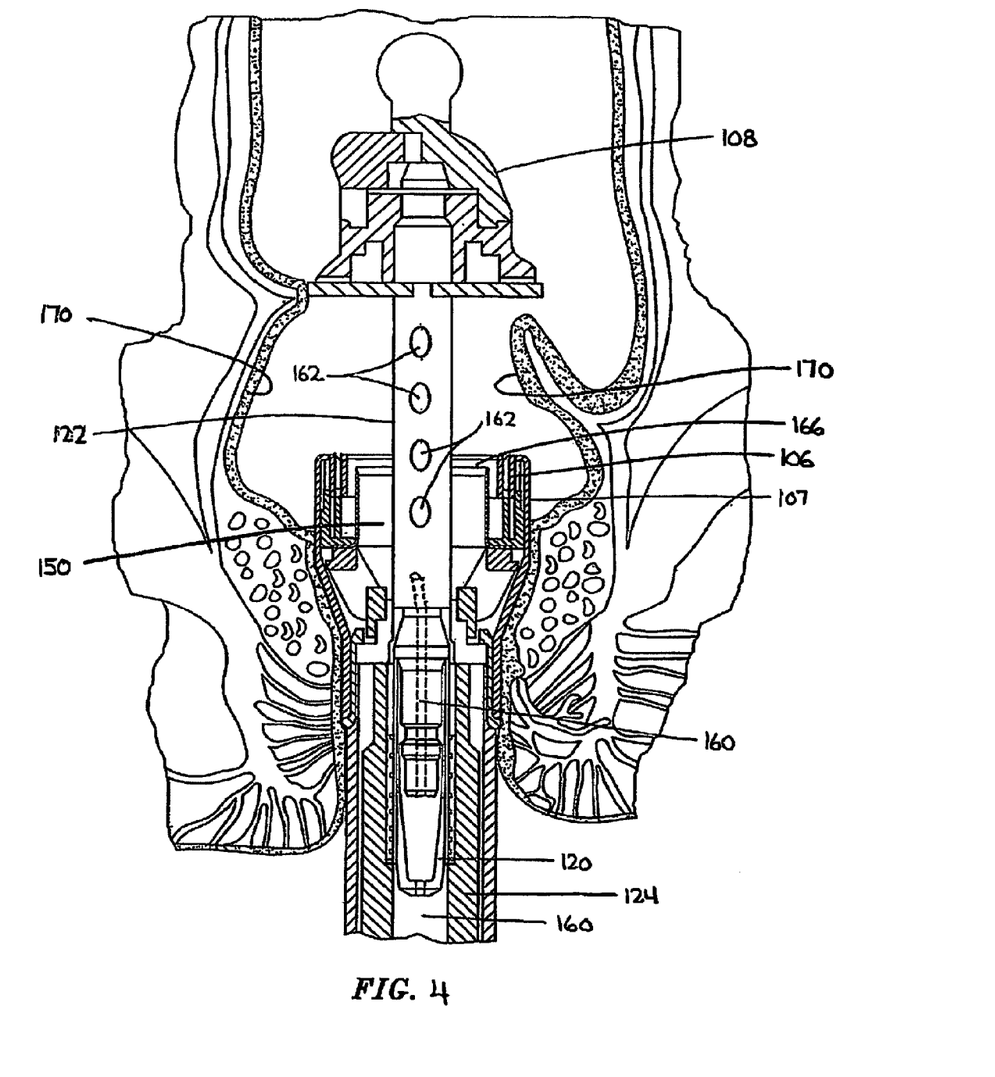
FIG. 4 illustrates a side cross-sectional cutaway view of the distal end of a circular surgical stapling apparatus positioned within the anus including a preferred means for drawing a vacuum within the shell assembly.

Referring to the embodiment of the circular stapling apparatus shown in FIG. 4, a vacuum channel 160 is provided through pusher back 124, anvil retainer 120 and anvil shaft 122. Depending on the particular stapler, these components may be hollow or solid. If the components are solid, channel 160 must be formed, i.e., molded or drilled, in the particular component. One or more vacuum openings 162 are provided in anvil shaft 122. Where only a single opening 162 is provided in anvil shaft 122, the opening should preferably be located in or near inner chamber 150. Openings 162 may be circular, oval, elongated channels 162*a* (FIG. 5), or any other configuration which permits air flow. A vacuum source (not shown) is fluidly connected to vacuum channel 160. As discussed above, the vacuum source may be external or a self-contained vacuum unit (not shown) supported in the handle assembly or elongated body of the apparatus. If an external vacuum source is provided, an inlet port (not shown) may be provided in the apparatus at any location proximal of anvil retainer 120 which communicates with vacuum channel 160. As discussed above with respect to FIG. 2, when a vacuum is drawn through vacuum channel 160, a low pressure region 166 is created in the inner chamber 150 of shell assembly 107 and in the area between shell assembly 107 and anvil assembly 108. This low pressure region functions to draw tissue from the inner walls 170 of the lumen about anvil shaft 122 of anvil assembly 108 and into inner chamber 150 of shell assembly 107. Tissue can then be severed and fastened in the manner discussed above.

Figure 5:
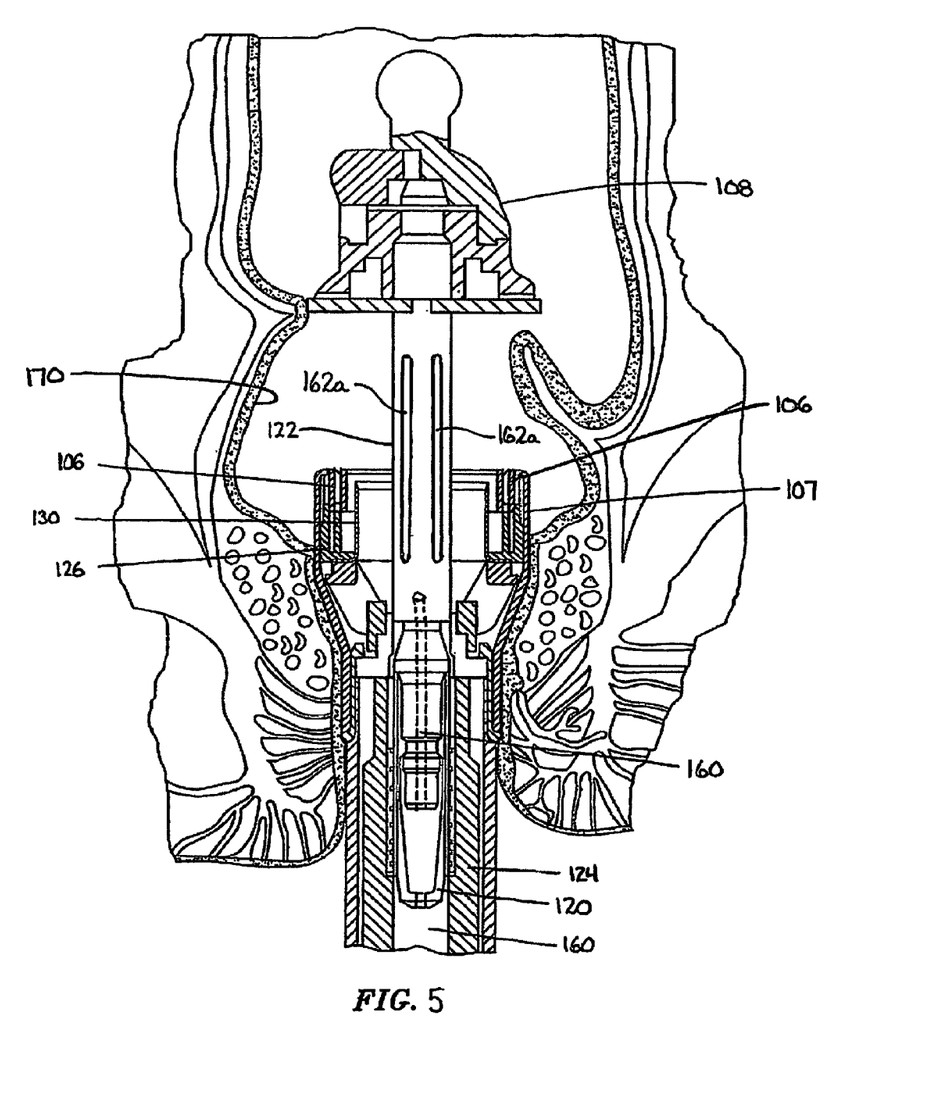
FIG. 5 illustrates a side cross-sectional cutaway view of the distal end of a circular surgical stapling apparatus positioned within the anus including another preferred means for drawing a vacuum with in the shell assembly.
Figure 6:
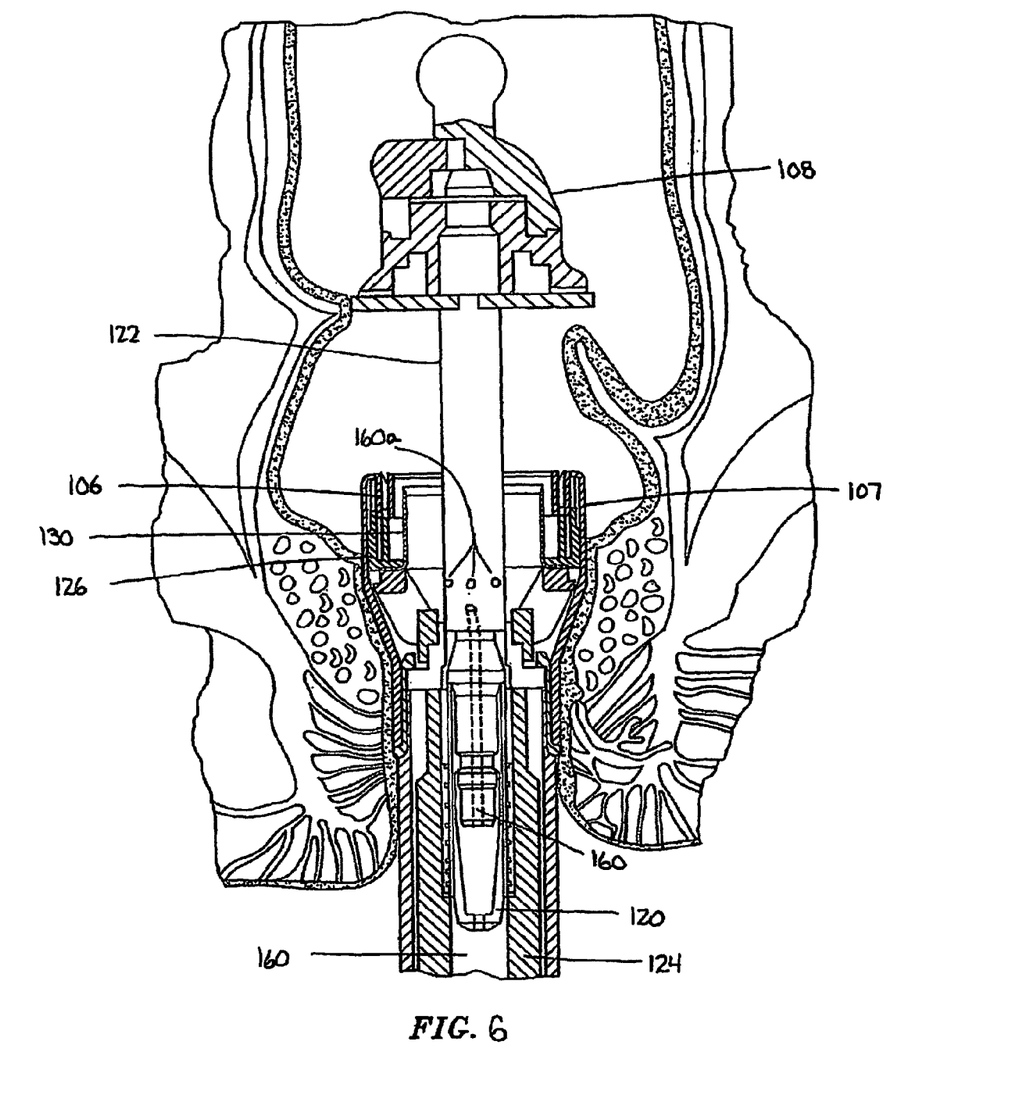
FIG. 6 illustrates a side cross-sectional cutaway view of the distal end of a circular surgical stapling apparatus positioned within the anus including another preferred means for drawing a vacuum within the shell assembly.

The circular stapling apparatus shown in FIG. 6 is similar to the apparatus shown in FIGS. 4 and 5 in that vacuum channel 160 is provided through pusher back 124, anvil retainer 120 and anvil shaft 122. However, vacuum channel 160 also includes an annular series of radial ports 160*a* formed through anvil shaft 122, which ports preferably are positioned within inner chamber 150 of shell assembly 107 when anvil assembly 108 and cartridge assembly 106 are in spaced relation. The apparatus operates in a manner similar to that described above. In this and other embodiments herein, ports can be fed by radial passageways extending from a main vacuum channel extending through anvil shaft 122.

Figure 7:
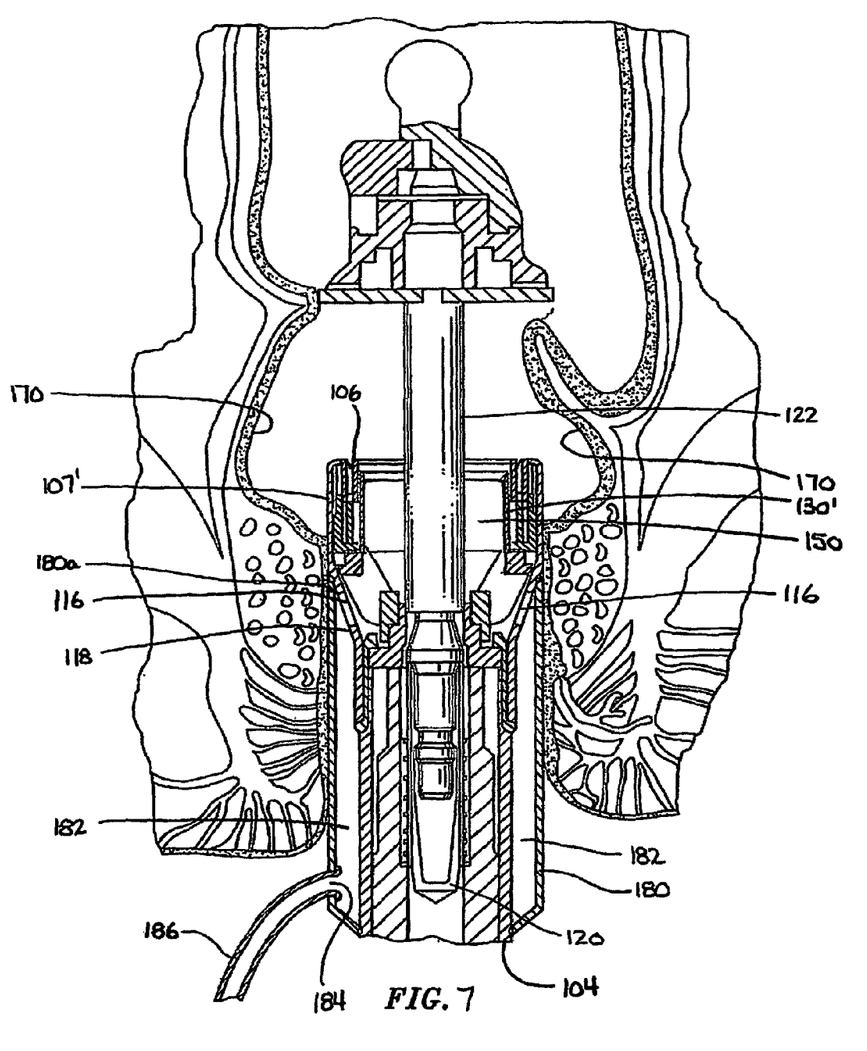
FIG. 7 is a side cross-sectional cutaway view of a circular surgical stapling apparatus shown in FIG. 1 positioned within the anus with another preferred embodiment of the presently disclosed vacuum device secured to the shell assembly of the surgical stapling apparatus.

Referring to FIG. 7, the vacuum device may include a hollow sleeve 180 which is positioned about the distal end of elongated body 104. The sleeve 180 defines a vacuum chamber 182 and includes an outlet port 184 which communicates with a vacuum tube 186. A distal end 180*a* of hollow sleeve 180 is positioned over conical portion 118 of shell assembly 107' such that holes and/or other apertures or clearances 116 of shell assembly 107' or shaft 104 are positioned within vacuum chamber 182. As such, when a vacuum is drawn through vacuum tube 186, a low pressure region is created in vacuum chamber 182 and within inner chamber 150 of shell assembly 107' as well as in the space defined between shell assembly 107' and anvil assembly 108. The low pressure region, as discussed above, draws mucosal tissue from the lumen walls 170 towards anvil shaft 122 and into inner chamber 150 of shell assembly 107.

Shell assembly 107' is substantially identical to shell assembly 107 shown in FIGS. 2-6 except that the diameter of annular knife blade 130' has been increased to define a larger unobstructed area within inner chamber 150. Spaces between other surrounding elements of the cartridge assembly radially exterior or outward of the annular knife blade 130' are preferably also compressed. As illustrated, the outer diameter of annular knife 130' is substantially equal to the inner diameter of cartridge 106. As such, a greater amount of tissue can be severed and retained within shell assembly 107' during use.

Figure 10:
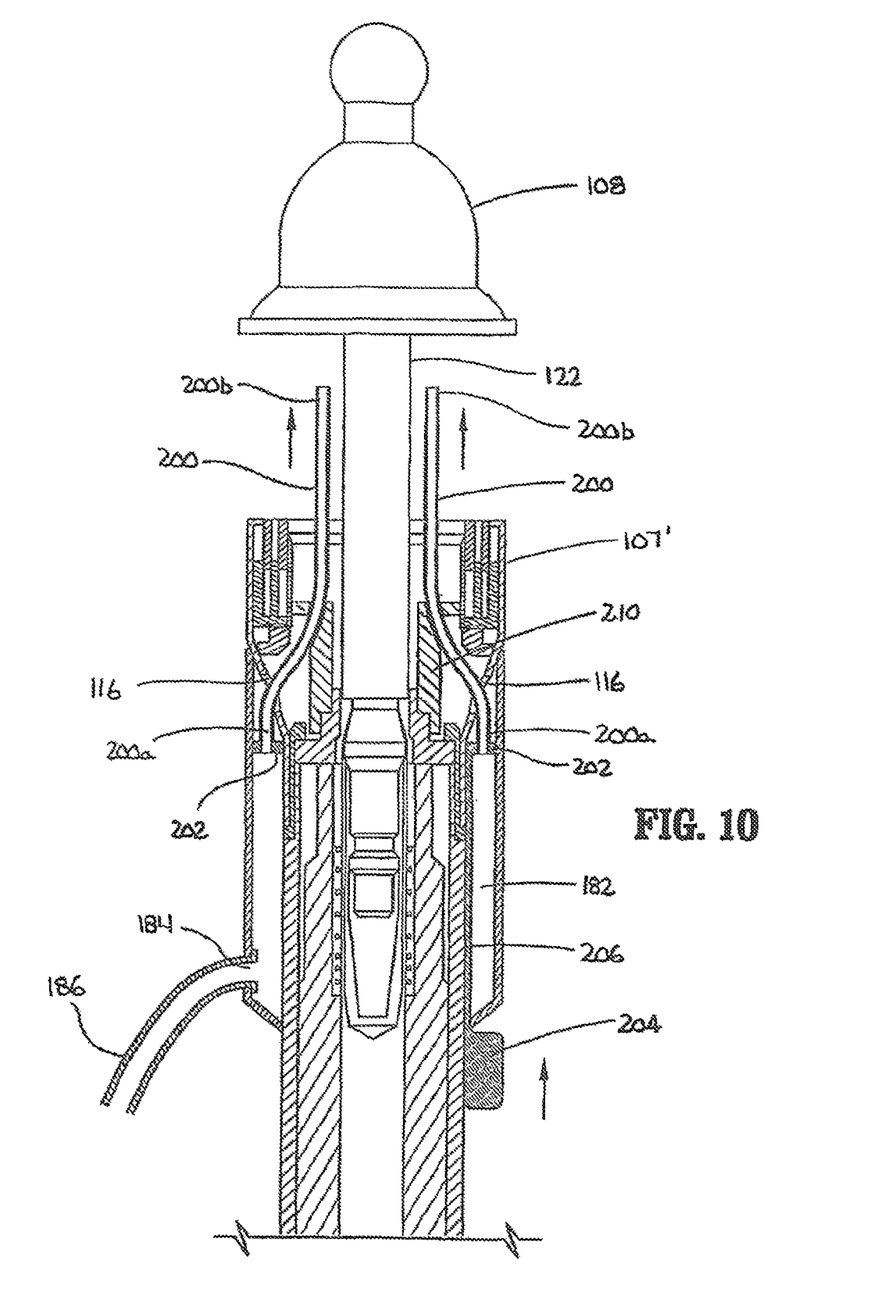
FIG. 10 is a side cross-sectional cutaway view of the surgical stapling apparatus shown in FIG. 8 with the vacuum device in the deployed position.
Figure 11:
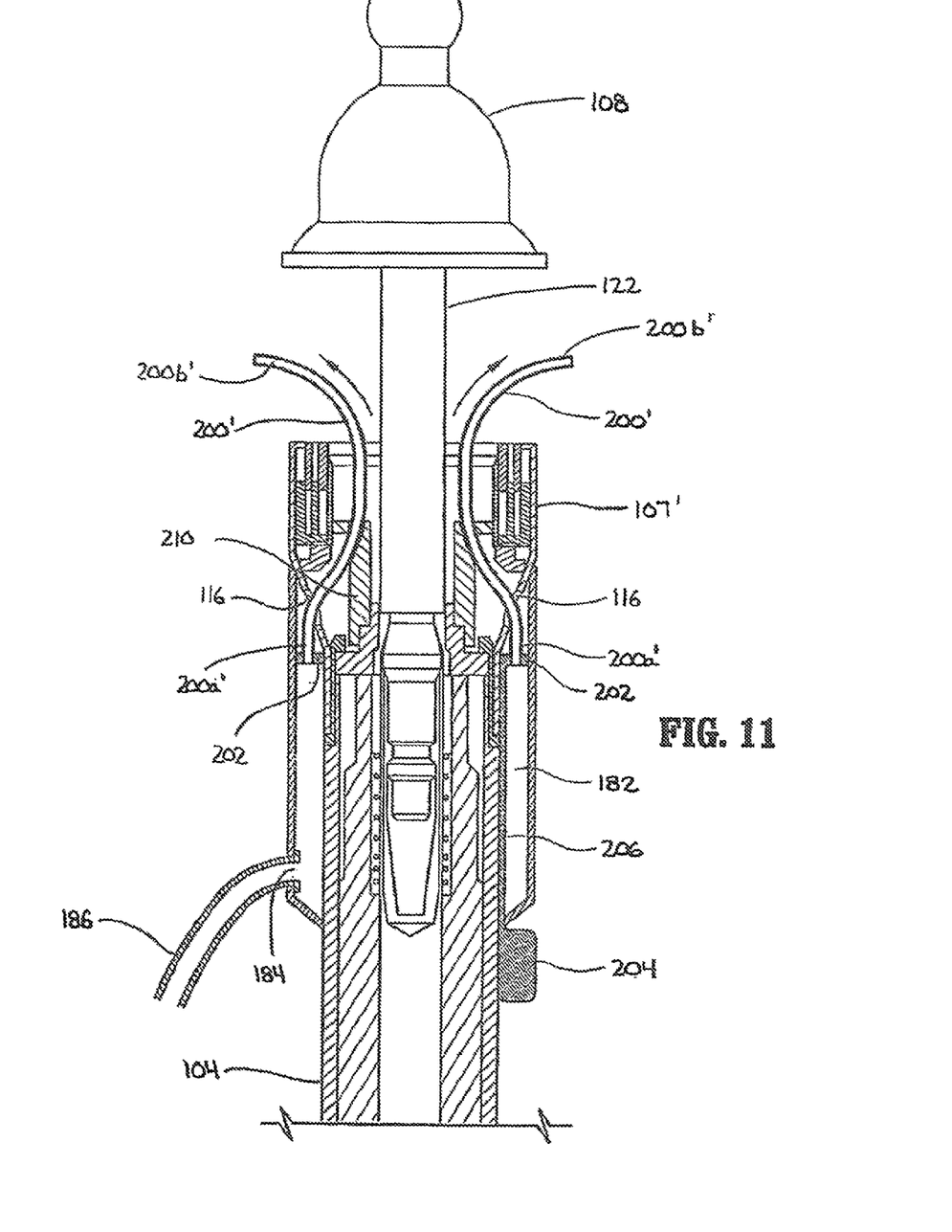
FIG. 11 is a side cross-sectional view of the circular stapling apparatus shown in FIG. 1 with another preferred embodiment of the presently disclosed vacuum device, in a deployed position, secured to the shell assembly of the surgical stapling device.

Referring to FIGS. 8-11, in addition to hollow sleeve 180, the vacuum device may include one or more vacuum tubes 200 which extend from within vacuum chamber 182 through holes 116 of shell assembly 107' into inner chamber 150 of shell assembly 107'. In one preferred embodiment, a plurality of vacuum tubes 200 are provided. Each vacuum tube includes a first end 200*a* secured to a slidable ring or manifold 202. Manifold 202 is slidably supported within vacuum chamber 182 and is fastened to a finger actuator 204 by a link 206. Link 206 may be integrally formed with manifold 202 and finger actuator 204. Alternately, these elements may be individually formed and secured together using known fastening techniques. Finger actuator 204 is slidable along an outer surface of elongated body 104 to move manifold 202 and vacuum tubes 200 between a retracted (non-deployed) position (FIG. 8) and an advanced (deployed) position (FIG. 10). Although finger actuator 204 is shown positioned on the elongated body 104, an appropriate linkage may be provided to position the finger actuator adjacent handles 112 (FIG. 1). Guide structure 210 may be provided within shell assembly 107' to direct vacuum tubes 200 through shell assembly 107'.

Figure 8:
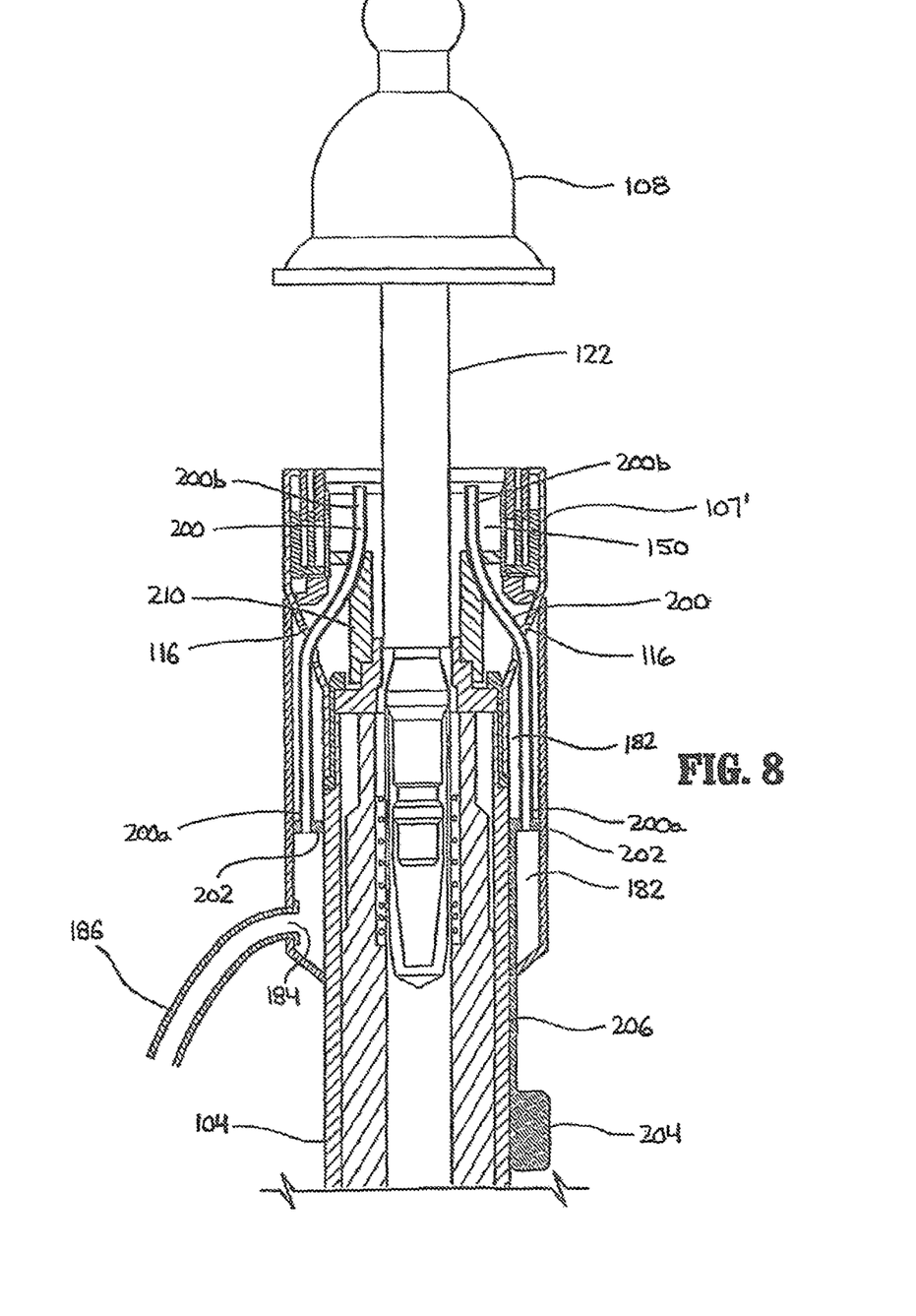
FIG. 8 is a side cross-sectional cutaway view of the circular surgical stapling apparatus shown in FIG. 1 with yet another preferred embodiment of the presently disclosed vacuum device, in a non-deployed position, secured to the shell assembly of the surgical stapling apparatus.
Figure 9:
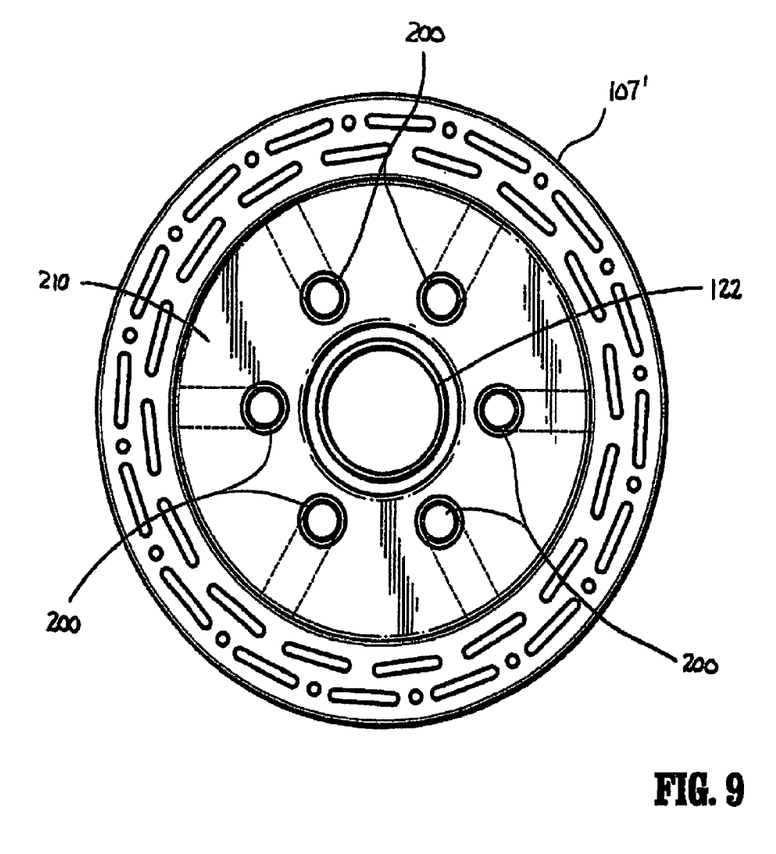
FIG. 9 is a top view of the surgical stapling apparatus shown in FIG. 8 with the anvil assembly removed.

Vacuum tubes 200 are preferably formed from a flexible material, e.g., plastic, rubber, metals, metal or plastic shape memory materials, etc. A second end of each vacuum tube 200 extends through a respective hole 116 in shell assembly 107' and is positioned within inner chamber 150 of shell assembly 107'. The location of the second end 200*b* of vacuum tube 200 can be repositioned by moving finger actuator 204 in relation to elongated body 104 from a position within inner chamber 150 to a position external of shell assembly 107'. It is envisioned that the length of vacuum tubes 200 may be selected to facilitate positioning of end 200*b* of vacuum tubes 200 at any location from within inner chamber 150 of shell assembly 107' to anvil assembly 108. Vacuum tubes 200 may also be of a length to engage tissue positioned radially outwardly of shell assembly 107'. In one preferred embodiment illustrated in FIG. 11, vacuum tubes 200' are formed of a resilient or shape-memory material which naturally curves radially outwardly of shell assembly 107' when vacuum tubes 200' are moved towards the deployed position. Tubes 200 are preferably of a length to engage tissue, e.g., mucosal tissue, defining the inner wall of a lumen, e.g., the anus. Tubes 200 may be deployed to engage tissue and, then, returned to the non-deployed position to pull tissue into the shell assembly.

It will be understood that various modifications may be made to the embodiments disclosed herein. For example, the vacuum devices disclosed herein may be incorporated into a circular surgical stapling apparatus not having vent holes in the shell assembly by providing a vacuum channel though the shell assembly of the circular stapling apparatus. Therefore, the above description should not be construed as limiting, but merely as exemplifications of preferred embodiments. Those skilled in the art will envision other modifications within the scope and spirit of the claims appended hereto.

The invention claimed is:

1. A surgical fastener applying apparatus comprising:
   a body portion;
   a shell assembly supported on a distal end of the body portion, the shell assembly having a cartridge assembly with staples;
   an anvil assembly movable in relation to the shell assembly between spaced and approximated positions, the anvil assembly comprising an anvil member and an anvil shaft extending proximally from the anvil member; and
   a vacuum device having a collar and a flexible conduit, the collar being dimensioned to be removably received about the shell assembly, the flexible conduit having a first end which communicates with a port in the collar and a second end for communicating with an external vacuum source.

2. A surgical fastener applying apparatus according to claim 1, wherein the shell assembly defines a vacuum channel.

3. A surgical fastener applying apparatus according to claim 2, wherein the vacuum channel is defined in a pusher back, in the anvil shaft, or both.

4. A surgical fastener applying apparatus according to claim 1, further including a pusher assembly configured and dimensioned for longitudinal movement through the body portion to facilitate ejection of a plurality of staples from the cartridge assembly.

5. A surgical fastener applying apparatus according to claim 4, wherein the pusher assembly includes pusher back and a staple driver, the pusher back and the stapler driver being in mechanical cooperation such that distal advancement of the pusher back causes distal advancement of the staple driver.

6. A surgical fastener applying apparatus according to claim 5, further including a vacuum channel that extends into the pusher back.

7. A surgical fastener applying apparatus according to claim 5 further including a knife member movable through the shell assembly, the pusher back and the knife member being in mechanical cooperation such that distal advancement of the pusher back causes distal advancement of the knife member.

8. A surgical fastener applying apparatus according to claim 7, wherein the knife member is annular in configuration.

9. A surgical fastener applying apparatus according to claim 2, further including an anvil retainer positioned within the shell assembly configured and dimensioned to receive the anvil shaft.

10. A surgical fastener applying apparatus according to claim 9, wherein the vacuum channel extends into the anvil retainer.

11. A surgical fastener applying apparatus according to claim 1, wherein the flexible conduit is integrally formed with the collar.

12. A surgical fastener applying apparatus according to claim 1, wherein the flexible conduit is secured to the collar by a connector.

13. A vacuum device comprising a resilient or elastic collar and a flexible conduit, the collar having a body defining a port and being dimensioned to be removably received about a shell assembly of a circular surgical stapling apparatus, the flexible conduit having a first end which is positioned to communicate with the port in the body of the collar and a second end for communicating with an external vacuum source.

14. A surgical fastener applying apparatus according to claim 13, wherein the flexible conduit is integrally formed with the collar.

15. A surgical fastener applying apparatus according to claim 13, wherein the flexible conduit is secured to the collar by a connector.

* * * * *